(12) United States Patent
Wingren

(10) Patent No.: US 11,617,897 B2
(45) Date of Patent: Apr. 4, 2023

(54) HEAD WORN ELECTRONIC DEVICE

(71) Applicant: BrainLit AB, Lund (SE)

(72) Inventor: Tord Wingren, Lund (SE)

(73) Assignee: BRAINLIT AB, Lund (SE)

( * ) Notice: Subject to any disclaimer, the term of this patent is extended or adjusted under 35 U.S.C. 154(b) by 0 days.

(21) Appl. No.: 16/917,063

(22) Filed: Jun. 30, 2020

(65) Prior Publication Data

US 2020/0324139 A1    Oct. 15, 2020

Related U.S. Application Data

(63) Continuation of application No. PCT/EP2019/077227, filed on Oct. 8, 2019.

(30) Foreign Application Priority Data

Nov. 21, 2018    (EP) .................................. 18207562

(51) Int. Cl.
*A61N 5/06* (2006.01)

(52) U.S. Cl.
CPC .... *A61N 5/0618* (2013.01); *A61N 2005/0626* (2013.01); *A61N 2005/0648* (2013.01); (Continued)

(58) Field of Classification Search
CPC .......... A61N 5/0618; A61N 2005/0663; A61N 2005/0626; A61N 2005/0648; (Continued)

(56) References Cited

U.S. PATENT DOCUMENTS

| 4,315,502 A | 2/1982 | Gorges |
| 6,350,275 B1 | 2/2002 | Vreman |

(Continued)

FOREIGN PATENT DOCUMENTS

| EP | 1642609 A1 | 4/2006 |
| EP | 3299871 A1 | 3/2018 |

(Continued)

OTHER PUBLICATIONS

Time and Frequency Measurements Using the Global Positioning System (https://tsapps.nist.gov/publication/get_pdf.cfm?pub_id=105004) (Year: 2001).*

(Continued)

*Primary Examiner* — Henry Luong
(74) *Attorney, Agent, or Firm* — Brundidge & Stanger, P.C.

(57) ABSTRACT

An electronic device is disclosed comprising: a frame configured to be worn on a head of a user; a first light emitter mounted on the frame and configured to illuminate a first eye of the user, wherein an intensity and a spectrum of the first light emitter is adjustable; a second light emitter mounted on the frame and configured to illuminate a second eye of the user, wherein an intensity and a spectrum of the second light emitter is adjustable; a clock; a memory configured to store a target light profile comprising time-resolved data on an amount of light to be accumulated over time by the first and/or second eye of the user, wherein the time-resolved data comprises information about spectrum and intensity; and a controller configured to control the intensity and spectrum of the first and second light emitter based on the time and the target light profile.

19 Claims, 4 Drawing Sheets

(52) U.S. Cl.
CPC ............... *A61N 2005/0652* (2013.01); *A61N 2005/0663* (2013.01)

(58) Field of Classification Search
CPC .... A61N 2005/0651; A61N 2005/0652; H05B 45/20; H05B 45/50; H05B 47/105; H05B 47/11; H05B 47/19; H05B 47/115
See application file for complete search history.

(56) References Cited

U.S. PATENT DOCUMENTS

| 2010/0110275 | A1* | 5/2010 | Mathieu | G02B 27/0075 |
| | | | | 382/117 |
| 2011/0221656 | A1* | 9/2011 | Haddick | H04N 5/2254 |
| | | | | 345/156 |
| 2011/0257467 | A1 | 10/2011 | Clegg | |
| 2015/0062323 | A1* | 3/2015 | Gustafsson | G06F 3/013 |
| | | | | 348/78 |
| 2017/0017299 | A1* | 1/2017 | Biedert | A61B 3/113 |
| 2017/0232225 | A1* | 8/2017 | Pedersen | A61M 21/00 |
| | | | | 607/88 |
| 2017/0312476 | A1 | 11/2017 | Woo | |
| 2018/0011360 | A1* | 1/2018 | Barrau | G02B 27/017 |
| 2019/0004325 | A1* | 1/2019 | Connor | G02B 27/0172 |

FOREIGN PATENT DOCUMENTS

| WO | 2012/146256 A2 | 11/2012 |
| WO | 2015120500 A1 | 8/2015 |
| WO | 2016133559 A1 | 8/2016 |

OTHER PUBLICATIONS

International Search Report from International Application No. PCT/EP2019/077227, dated Nov. 5, 2019.
Extended European Search Report dated May 27, 2019.
Written Opinion of International Preliminary Searching Authority dated (PCT Rule 66), dated Mar. 3, 2020.

* cited by examiner

HEAD WORN ELECTRONIC DEVICE

TECHNICAL FIELD

The present invention relates to an electronic device configured to be worn on a head of a user.

BACKGROUND OF THE INVENTION

It is known that exposure to light is very important for the well-being of humans and animals. In today's society, artificial lights are very common and much development has been made in order to produce light sources that can reproduce natural lighting environments. For instance, there exists light sources that aim to reproduce a bright sunny day in the indoor environment in, for example, an office. It is also possible to treat different health conditions, such as sleep disorders or seasonal affective disorders, by adjusting the spectral content and the intensity of light sources.

Different individuals, however, are affected in different ways by the lighting environment, and they therefore have different needs when it comes to lighting conditions. Some individuals, for example, are more sensitive than others to blue components in light, which is known to affect health aspects such as sleep quality. Therefore, lighting systems is often configured to suit as many individuals or activities as possible. However, this may result in conflicting settings of light sources in a room, and it can therefore be problematic or even impossible to correctly adjust each light source. Lighting system can therefore use averaged settings for the light sources based on individual settings. This typically results in a light environment which is poorly adapted to the individuals' preferences.

Thus, there is a need for a more flexible light exposure system which can be automatically and actively adapted to the preferences of individual humans or animals.

SUMMARY OF THE INVENTION

In view of the above, it is an objective of the present inventive concept to provide an electronic device configured to be worn on a head of a user.

It is an objective to mitigate, alleviate or eliminate one or more of the above-identified deficiencies in the art and disadvantages singly or in any combination and solve at least the above mentioned problem.

According to a first aspect an electronic device is provided. The electronic device comprises: a frame configured to be worn on a head of a user; a first light emitter mounted on the frame and configured to illuminate a first eye of the user, wherein an intensity and a spectrum of the first light emitter is adjustable; a second light emitter mounted on the frame and configured to illuminate a second eye of the user, wherein an intensity and a spectrum of the second light emitter is adjustable; a clock configured to determine a time; a memory configured to store a target light profile comprising time-resolved data on an amount of light to be accumulated over time by the first and/or second eye of the user, wherein the time-resolved data comprises information about spectrum and intensity; and a controller configured to control the intensity and spectrum of the first and second light emitter based on the time and the target light profile.

The wording "memory" should, within the context of this application, be construed as a computer-readable memory, such as ROM, RAM, SRAM, DRAM, CMOS, FLASH, DDR, SDRAM, or some other memory technology.

The wording "target light profile" should, within the context of this application, be construed as information relating to a preferred light dose or a preferred amount of light that the user should accumulate over time. The preferred light dose/preferred amount of light may be different for different wavelengths.

By means of the present electronic device it is possible to illuminate the eye of a user with a personalized light, adapted to a need of the user. Further, by adjusting the spectrum and intensity of the light emitters based on the time and the target light profile, an electronic device which actively and automatically controls the first and/or second light source is allowed. Thereby, the accumulation of light that the individual has been exposed to may be aligned with the preferred amount of light that the user should accumulate over time. The personalized light may be adapted to improve health aspects of the user. Thus, the present electronic device allows for a user-specific lighting condition, which may automatically be adapted such that a well-being for the user is improved. An advantage of the electronic device comprising a clock configured to determine the time is that the control of the light emitters may be time-dependent. Thereby, the light exposure of the user may be time-dependent. It is to be understood that the wordings "light exposure of the user" and "light exposure of the first and/or second eye of the user" may be used interchangeably within the context of this application. The electronic device may thereby be used to subject the user to circadian lighting, such that the light exposure of the user follows the circadian rhythm of the user.

An advantage of the electronic device comprising a memory comprising time-resolved data on an amount of light to be accumulated by the first and/or second eye of the user is that the light exposure of the user may be aligned with the target light profile over time.

The controller may be further configured to individually control the first and second light emitters.

An advantage of the controller being configured to individually control the first and second light emitters is that the first and second light emitters may emit light of different intensity and/or spectral content. Thereby, the electronic device may adjust the intensity and/or the spectral content of the first and second light emitter individually in order to compensate for spatial differences in ambient light.

The first and/or second light emitter may be adjustably mounted on the frame.

An advantage of the first and/or second light emitter being adjustably mounted on the frame is that a position of the first and/or second light emitter may be adjusted. A further advantage of the first and/or second light emitter being adjustably mounted on the frame is that a direction of light emitted from the first and/or second light emitter may be adjusted. A more flexible electronic device may thereby be allowed.

Thereby, the electronic device may be adjusted for different users having different face shapes and/or eye characteristics by adjusting the position of the light emitters and/or the direction of light emitted from the light emitters. Adjusting the positions of the light emitters and/or the directions of light emitted from the light emitters may also allow for a more complex adjustment of the light exposure of the user.

The electronic device may further comprise: a first driver configured to adjust the first light emitter and/or a second driver configured to adjust the second light emitter; and wherein the controller may be further configured to control the first and/or second driver.

An advantage of the electronic device further comprising a first driver configured to adjust the first light emitter and/or a second driver configured to adjust the second light emitter is that it may allow for electronic adjustment of the first and/or second light emitter. Thereby, the positions of the light emitters and/or the direction of light emitted from the light emitters may be adjusted while the user is wearing the electronic device, which may allow for a more versatile and flexible adjustment of the first and/or second light emitter.

The target light profile may further comprise time-resolved data on angle of incidence for light to be received by the first and/or second eye of the user; and wherein the controller may be further configured to control the first and/or second driver based on the time-resolved data on angle of incidence.

The wording "angle of incidence" should, within the context of this application, be construed as an angle at which light emitted from a light emitter impinges on the eye of the user.

An advantage of the target light profile comprising time-resolved data on angle of incidence for light to be received by the first and/or second eye of the user is that a direction from which the preferred light dose is to be accumulated may be time-dependent.

An advantage of the controller being further configured to control the first and/or second driver based on the time-resolved data on angle of incidence is that a direction from which the light illuminates the first and/or second eye may be time-dependently adjusted.

The electronic device may further comprise: a light sensor configured to sense ambient light; and wherein the controller may be further configured to adjust the intensity and spectrum of the first and/or second light emitter based on the sensed ambient light.

The wording "ambient light" should, within the context of this application, be construed as ambient light reaching an eye of the user.

An advantage of the electronic device further comprising a light sensor configured to sense ambient light is that it may allow the electronic device to adjust the spectrum and intensity of light emitted by the light emitters according to the ambient light sensed by the light sensor. Thereby, it allows the electronic device to determine a contribution of the ambient light to the light exposure of the user.

An advantage of the controller being further configured to adjust the intensity and spectrum of the first and/or second light emitter based on the sensed ambient light is that it may allow for an improved alignment between the light exposure of the user and the target light profile.

The electronic device may further comprise optics mounted to the frame, wherein the optics are configured to filter and/or refract ambient light.

An advantage of the electronic device comprising optics configured to filter ambient light is that predetermined wavelengths of the ambient light may be reduced in intensity. Thereby, hazardous wavelength reaching the eye of the user may be reduced.

A further advantage of the electronic device comprising optics configured to filter ambient light is that it may allow for an improved alignment between the light exposure of the user and the target light profile.

An advantage of the electronic device comprising optics configured to refract ambient light is that it may allow for correction of a defect of vision of the user.

The electronic device may further comprise an eye sensor configured to determine eye characteristics of the first and/or second eye of the user.

The wording "eye characteristics" should, within the context of this application, be construed as features of the eye of the user. For instance, a movement pattern of the eye, a size of a pupil of the eye, features of a retina in the eye, and an iris of the eye may be such features.

An associated advantage is that the operation of the electronic device may be adjusted based on the determined eye characteristics of the first and/or second eye of the user.

The controller may be further configured to, based on the eye characteristics, determine an identity of the user. Subsequent to determining the identity of the user, the controller may retrieve the target light profile of the identified user from a memory and/or a remote server. A more flexible electronic device may thereby be allowed. Further, an automatic or easier setup of the electronic device may thereby be allowed.

An advantage of the controller being further configured to, based on the eye characteristics, determine an identity of the user is that it may allow for automatic identification of the user. Thereby, it may be easier to share the electronic device between a plurality of different users, leading to reduced costs associated with procurement of electronic devices for a plurality of different users.

The controller may be further configured to, based on the eye characteristics, adjust the target light profile.

An advantage of adjusting the target light profile based on the eye characteristics is that it may allow for an improved target light profile of the user. Thereby, an improved well-being of the user may be achieved by aligning the light exposure of the user to the improved target light profile.

The electronic device may further comprise a transceiver configured to communicate with one or more of: a server; an external sensor; and an external light emitter.

An advantage of the electronic device further comprising a transceiver configured to communicate with a server is that it may allow for storing data relating to light exposure of the user and/or the target light profile on the server. Thereby, it simplifies the sharing of the electronic device between different users and it facilitates central control of the electronic device. It may also allow for a less complex electronic device, thereby reducing costs associated with the electronic device.

An advantage of the electronic device further comprising a transceiver configured to communicate with an external sensor is that data relating to events relating to the user and/or the environment of the user sensed by the external sensor may be included in the target light profile of the user. The data sensed by the external sensor may further be used to set the intensity and spectrum of the light emitters. Thereby, an improved alignment between the light exposure of the user and the target light profile may be allowed.

An advantage of the electronic device further comprising a transceiver configured to communicate with an external light emitter is that data relating to the external light emitter may be used to adjust the first and/or second light emitter. Thereby, it may be possible to adjust the first and/or second light emitter to compensate for an intensity and spectrum of light emitted by the external light emitter.

The electronic device may further comprise sensors configured to sense one or more of: a movement of the user; a position of the user; and a health status of the user.

An advantage of the electronic device further comprising sensors configured to sense a movement of the user is that it may allow the electronic device to adjust the intensity and spectrum of the first and/or second light emitter depending on a movement pattern of the user.

A further advantage of the electronic device further comprising sensors configured to sense a movement of the user is that it may allow the electronic device to sense a movement resulting from a specific setting of the intensity and spectrum of the first and/or second light emitter. Thereby, the electronic device may stimulate the user towards a desired movement by adjusting the first and/or second light emitter.

An advantage of the electronic device further comprising sensors configured to sense a position of the user is that it may allow the electronic device to adjust the intensity and spectrum of the first and/or second light emitter based on the position of the user. Thereby, the intensity and spectrum of the first and/or second light emitter may be adjusted based on a geographical position of the user.

An advantage of the electronic device further comprising sensors configured to sense a health status of the user is that it may allow the electronic device to sense the health status resulting from a specific setting of the intensity and spectrum of the first and/or second light emitter. Thereby, the electronic device may determine how the user may be stimulated towards a desired health status by adjusting the first and/or second light emitter.

A further advantage of the electronic device further comprising sensors configured to sense a health status of the user is that it may allow sensing of an impact of the intensity and spectrum of the first light emitter, the second light emitter, and/or the ambient light on the health status. Thereby, the target light profile may be gradually improved.

A further advantage of the electronic device further comprising sensors configured to sense a health status of the user is that it may allow the electronic device to adjust the intensity and spectrum of the first and/or second light emitter based on the health status of the user. Thereby, the electronic device may adjust the intensity and spectrum of the first and/or second light emitter to encourage the user to rest in case the electronic device determines that the user is sick.

The controller may be further configured to determine a size of the pupil of the first and/or second eye of the user based on the eye characteristics.

An advantage of the controller being further configured to determine a size of the pupil of the first and/or second eye of the user based on the eye characteristics is that it may allow the electronic device to adjust the first and/or second light emitter based on the size of the pupil of the first and/or second eye of the user.

A further advantage of the controller being further configured to determine a size of the pupil of the first and/or second eye of the user based on the eye characteristics is that it may allow for an improved determination of an amount of light that the first and/or second eye of the user has been exposed to. Such information may be used by the controller may result in an improved active and automatic control of the first and/or second light emitter. For example, for a large size of the pupil, the preferred amount of light that the user should accumulate over time may be reached for a reduced intensity of the first and/or second light emitter, thereby resulting in a reduced power consumption of the electronic device. Hence, the size of the pupil of the user may be used by the controller in order to improve the control of the first and/or second light emitter, which may thereby result in a reduced power consumption of the electronic device.

The controller may be further configured to determine an optical transfer function of the first and/or the second eye of the user based on the eye characteristics.

An advantage of the controller being further configured to determine an optical transfer function of the first and/or the second eye of the user based on the eye characteristics is that it may allow for an improved determination of an amount of light that has reached the retina(s) and/or other photoreceptor cells of the first and/or second eye of the user. Such information may be used by the controller and may result in an improved active and automatic control of the first and/or second light emitter. For example, for a high light transmission through an eye, the preferred amount of light that the user should accumulate over time may be reached using a reduced intensity of the first and/or second light emitter, thereby resulting in a reduced power consumption of the electronic device. Hence, the optical transfer functions of the first and/or second eye of the user may be used by the controller in order to improve the control of the first and/or second light emitter, which may thereby result in a reduced power consumption of the electronic device.

The electronic device may further comprise a brain sensor configured to determine brain characteristics of the user.

The brain sensor may be arranged on the head of the user. The brain sensor may comprise an electrode. The brain sensor may comprise an electroencephalography (EEG) sensor. The brain sensor may comprise a plurality of EEG sensors.

The wording "brain characteristics" should, within the context of this application, be construed as characteristics of an electrical activity of the brain. Such electrical activity is commonly categorized as brain waves. The brain characteristics may, e.g., be a frequency and/or an amplitude of the brain waves. The brain characteristics may be associated with an activity of the user.

An advantage of the electronic device further comprising a brain sensor configured to determine brain characteristics of the user is that it may allow the electronic device to collect information relating the brain characteristics with light emitted from the first and/or second light emitter. For example, the controller may adjust the first and/or second light emitter and determine how certain brain characteristics are affected. Thus, the electric device may control the first and/or second light emitter in order to affect certain brain characteristics. For example, in case the brain characteristics indicate that the user is drowsy, the first and/or second light emitter may be controlled to emit more blue light in order to raise the alertness of the user. An improved active and automatic control of the first and/or second light emitter may thereby be allowed.

The controller may be further configured to determine a state of the brain of the user based on the brain characteristics.

The state of the brain may be a state of consciousness of the user. The state of the consciousness of the user may be related to the level of, e.g., sleep, alertness, focus etc. The state of consciousness may be determined based on the brain characteristics, e.g. the frequency and/or amplitude of the brain waves. Brain waves are commonly categorized with respect to frequency and/or amplitude. Examples of brain wave categories comprise alpha waves, beta waves, theta waves, and delta waves. For example, alpha waves may typically be dominant during relaxation/reflection; beta waves may be related to a strongly engaged mind; theta waves may be related to daydreaming; delta waves may be associated with deep sleep. A skilled person knows that further categories of brain waves, such as gamma waves, may also be used to determine the state of the brain of the user.

An advantage of the controller being further configured to determine a state of the brain of the user based on the brain characteristics is that a the first and/or second light emitter may be controlled based on the determined state of the brain.

For example, in case the controller determines that a user is daydreaming (theta waves), the first and/or second light emitter may be controlled to help the user become focused (beta waves). An improved active and automatic control of the first and/or second light emitter may thereby be allowed. A skilled person realizes that other sensors, such as motion sensors, may be used to determine the type of activity the user is currently engaged in and compare with the state of the brain in order to further improve the automatic control of the first and/or second light emitter.

The controller may be further configured to control the first and/or second light emitter based on the brain characteristics. The controller may be further configured to control the first and/or second light emitter based on the determined state of the brain.

An advantage of the controller being further configured to control the first and/or second light emitter based on the brain characteristics is that it may allow the electronic device to adapt the light emitted from the first and/or second light emitter to better suit the current state of the brain of the user. An improved active and automatic control of the first and/or second light emitter may thereby be allowed.

The optics may comprise a display, wherein an intensity and a spectrum of each of light emitters associated with the display may be adjustable. The controller may be further configured to control the intensity and spectrum of each of the light emitters associated with the display based on the time and the target light profile. The controller may be further configured to control the intensity and the spectrum of each of the light emitters associated with the display further based on the eye characteristics. The display may be configured to display information to the user.

At times when the display is not in use, for example that it is currently not showing information, the light emitters associated with the display may be used in a similar manner as the first and/or second light emitter of the device. Thus, the light emitters associated with the display may thereby be configured to illuminate the first and/or second eye of the user and to display information for the user. The number of light emitters required by the device may thereby be reduced.

A further scope of applicability of the present disclosure will become apparent from the detailed description given below. However, it should be understood that the detailed description and specific examples, while indicating preferred variants of the present inventive concept, are given by way of illustration only, since various changes and modifications within the scope of the inventive concept will become apparent to those skilled in the art from this detailed description.

Hence, it is to be understood that this inventive concept is not limited to the particular component parts of the electronic device described as such may vary. It is also to be understood that the terminology used herein is for purpose of describing particular variants only, and is not intended to be limiting. It must be noted that, as used in the specification and the appended claims, the articles "a", "an", "the", and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings do not exclude other elements.

BRIEF DESCRIPTION OF THE DRAWINGS

The above and other aspects of the present invention will now be described in more detail, with reference to appended drawings showing variants of the present disclosure. The figures should not be considered limiting the inventive concept to the specific embodiment; instead they are used for explaining and understanding the inventive concept.

As illustrated in the figures, the sizes of layers and regions are exaggerated for illustrative purposes and, thus, are provided to illustrate the general structures of variants of the present disclosure. Like reference numerals refer to like elements throughout.

DETAILED DESCRIPTION OF THE PREFERRED EMBODIMENT

The present inventive concept will now be described more fully hereinafter with reference to the accompanying drawings, in which currently preferred variants of the inventive concept are shown. This inventive concept may, however, be implemented in many different forms and should not be construed as limited to the variants set forth herein; rather, these variants are provided for thoroughness and completeness, and fully convey the scope of the present inventive concept to the skilled person.

An electronic device according to the present disclosure will now be described with reference to FIG. 1-FIG. 7.

Figure 1:
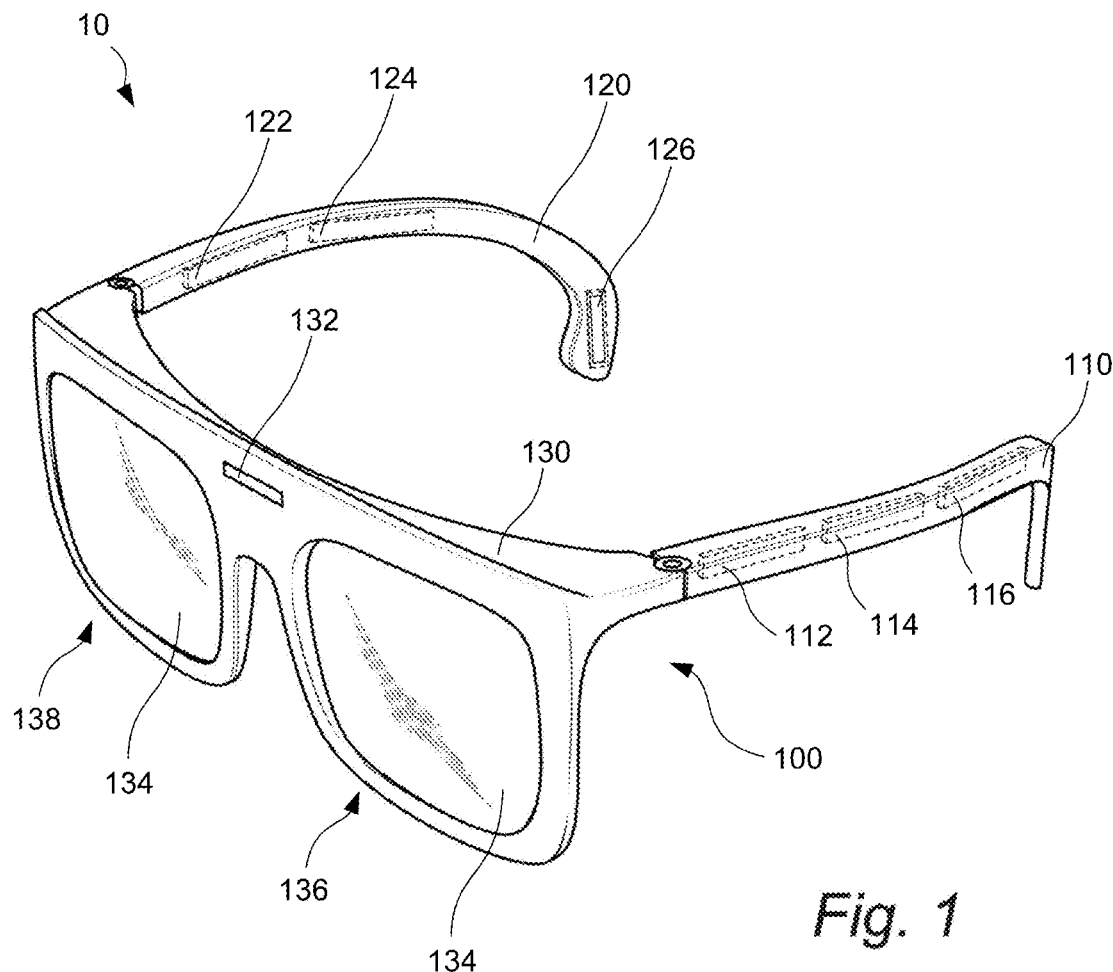
FIG. 1 illustrates an isometric view of an electronic device.

FIG. 1 illustrates an isometric view of an electronic device 10. The electronic device 10 comprises a frame 100 configured to be worn on a head of a user. The frame 100 comprises a rim 130. The frame 100 further comprises a first temple 110 and a second temple 120. The first temple 110 is connected to a first side of the rim 130. The second temple 120 is connected to a second side of the rim 130. The first side of the rim 130 and the second side of the rim 130 are connected by a bridge. The frame 100 may further comprise nose pads. The frame 100 may further comprise a first opening 136 and/or a second opening 138 for incoming ambient light.

A skilled person realizes that other frames may be used for the electronic device 10. For instance, the frame 100 may comprise an elastic strap instead of temples as shown in FIG. 1. The frame 100 may be configured to fit tightly around the eyes of the user. A tight fit of the frame 100 may reduce an amount of ambient light entering through gaps between the frame 100 and the user.

The electronic device 10 further comprises a first light emitter 142 mounted on the frame 100 and configured to illuminate a first eye of the user. An intensity and a spectrum of the first light emitter 142 are adjustable.

The electronic device 10 further comprises a second light emitter 144 mounted on the frame 100 and configured to illuminate a second eye of the user. An intensity and a spectrum of the second light emitter 144 are adjustable.

The first and second light emitter 142, 144 may comprise a plurality of light sources. The light sources of the plurality of light sources may be configured to emit light of different spectra. The spectra of light emitted by the first and second light emitters 142, 144 may be adjusted by adjusting the spectra of the plurality of light sources of respective light emitter 142, 144. It is to be understood that the electronic device 10 may comprise a further number of light emitters configured to illuminate the first and second eyes of the user.

The electronic device 10 further comprises a controller 112 configured to control the intensity and spectrum of the first and second light emitter 142, 144. The controller 112 may be configured to individually control the first and second light emitters 142, 144. For example, the controller 112 may compensate for non-uniform ambient light conditions by individually controlling the first and second light emitter 142, 144. It is to be understood that, in case the electronic device 10 comprises a further number of light emitters, the controller 112 may be configured to individually control each light emitter.

The first and/or second light emitter 142, 144 may be adjustably mounted on the frame 100. For instance, the direction and/or position of the light emitters 142, 144 may be adjustable. Therefore, it may allow the electronic device 10 to be adjustable to different users. It may also allow the electronic device 10 to imitate natural lighting conditions. For instance, a blue sky may be imitated by letting blue light impinge from a position above the eyes of the user.

The electronic device 10 may further comprise a first driver configured to adjust the first light emitter 142 and a second driver configured to adjust the second light emitter 144. An example of a light emitter and a driver will be described in relation to FIG. 4. The controller 112 may be further configured to control the first and/or second driver. A driver may be configured to control a position of a light emitter 142, 144 and/or a direction of light emitted by a light emitter 142, 144. Thereby, it may allow the electronic device 10 to imitate evolving natural lighting conditions. For example, the electronic device 10 may imitate a position of a sun in the sky.

The electronic device 10 may further comprise a clock 122 configured to determine a time. The clock 122 may be further configured to determine a date. The electronic device 10 may thereby imitate lighting conditions of a sunset at a time where the sun usually sets. The electronic device 10 may further comprise a memory 114 configured to store a target light profile comprising time-resolved data on an amount of light to be received by the first and/or second eye of the user. The target light profile may be associated with the user. The target light profile may comprise an optical transfer function of the eye of the user. The optical transfer function of the eye may describe how an intensity and a spectrum of light impinging on the eye relates to an intensity and a spectrum of light reaching a retina in the eye. The target light profile may comprise a chemical transfer function of the eye of the user. The chemical transfer function of an eye may describe a relation between an intensity and spectrum of light reaching a retina in the eye and a generation of hormones. The time-resolved data may comprise information about spectrum and intensity.

The controller 112 may be further configured to adjust the intensity and spectrum of the first and/or second light emitter 142, 144 based on the time and the target light profile.

The target light profile may further comprise time-resolved data on angle of incidence for light to be received by the first and/or second eye of the user. The controller 112 may be further configured to control the first and/or second driver based on the time-resolved data on angle of incidence.

The electronic device 10 may further comprise a light sensor 132 configured to sense ambient light. The controller 112 may be further configured to adjust the intensity and spectrum of the first and/or second light emitter 142, 144 based on the sensed ambient light. The light sensor 132 may sense a spectrum and/or an intensity of ambient light. The controller 112 may adjust the intensity and spectrum of the first and/or second light emitter 142, 144 based on time of day and/or date.

The electronic device 10 may further comprise optics 134 mounted to the frame 100. The optics 134 may be configured to filter and/or refract ambient light. For example, the optics 134 may be one or more of a blue-light filter, an intensity-reducing filter, a corrective lens, and a polarizing filter. The optics 134 may be adjustable. For instance, an intensity reduction of an intensity-reducing filter may be adjustable.

Figure 5:
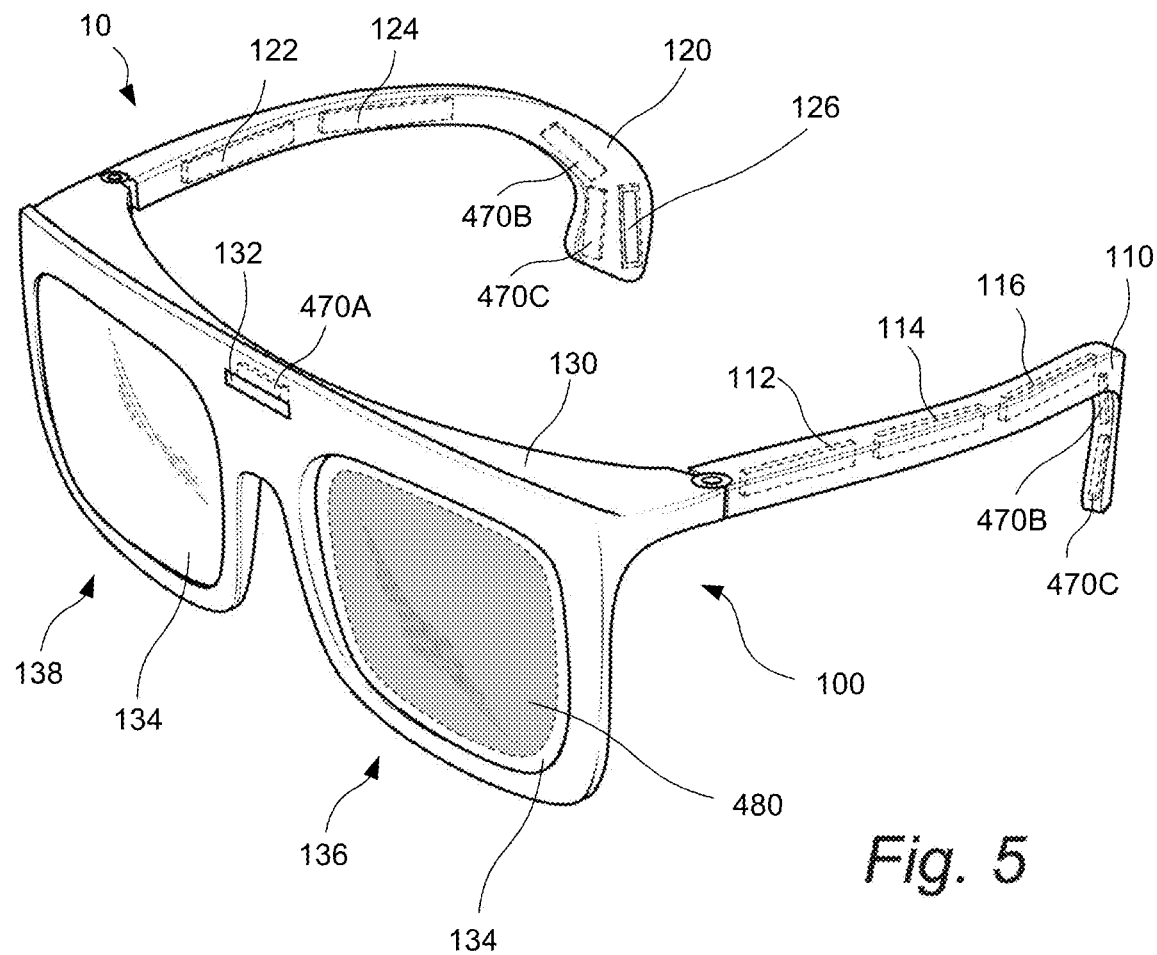
FIG. 5 illustrates an isometric view of an electronic device comprising a brain sensor and a display.
Figure 6:
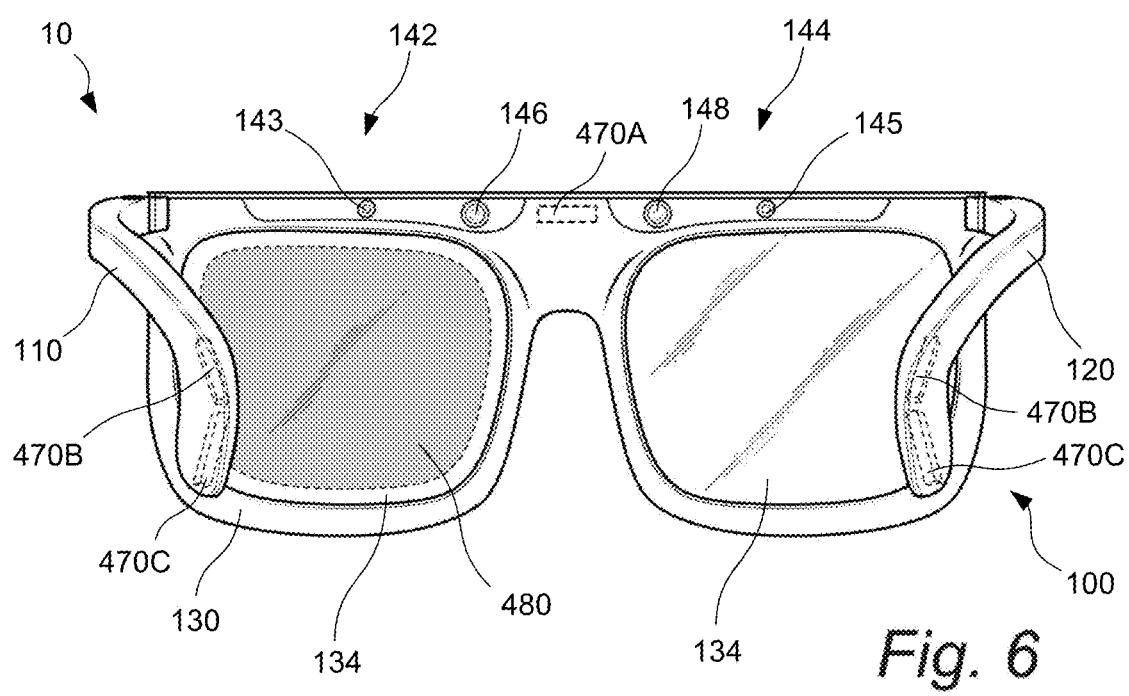
FIG. 6 illustrates an inside of the frame of the electronic device comprising a brain sensor and a display.
Figure 7:
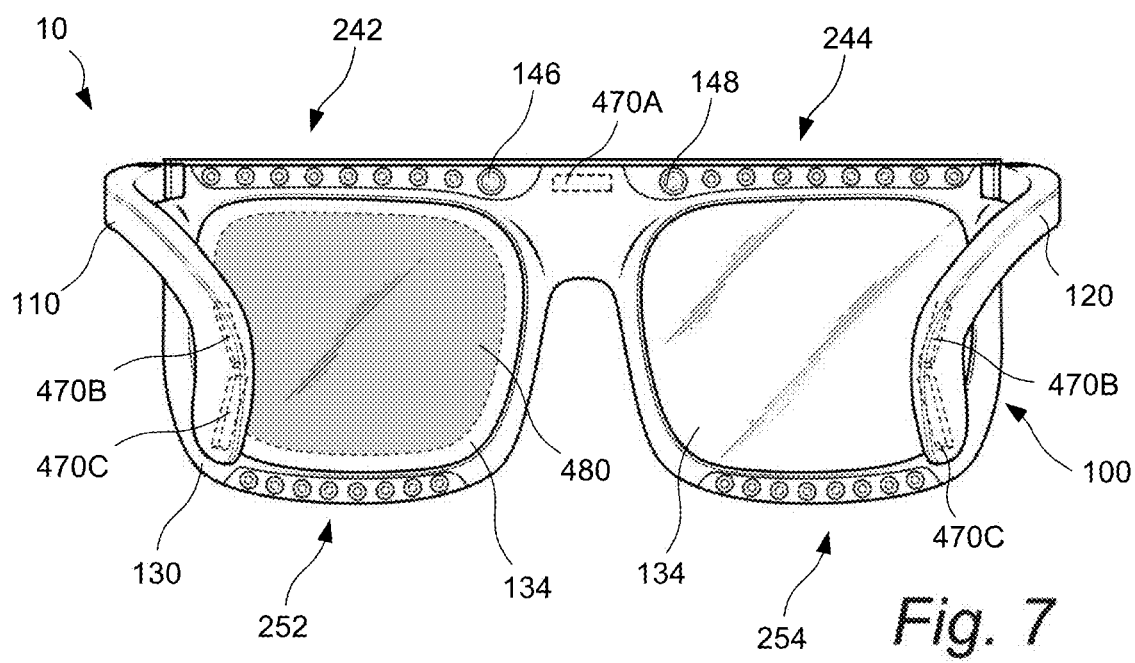
FIG. 7 illustrates an inside of the frame of the electronic device comprising a brain sensor and a display.

The optics 134 may comprise a display 480 as exemplified in FIG. 5-FIG. 7. An intensity and a spectrum of each of light emitters associated with the display 480 may be adjustable. The controller 112 may be further configured to control the intensity and spectrum of each of the light emitters associated with the display 480 based on the time and the target light profile. The controller 112 may be further configured to control the intensity and the spectrum of each of the light emitters associated with the display 480 further based on the eye characteristics. The display 480 may be configured to display information to the user. The display 480 in FIG. 5-FIG. 7 is specifically shown to be comprised in the left optic 134, however, it is to be understood that the display 480 may alternatively be comprised in the right optic 134. Additionally, both the left and the right optic 134 may comprise a display 480.

At times when the display 480 is not in use, for example in case the display 480 is not currently showing information, the light emitters associated with the display may be used in a similar manner as the first and/or second light emitter 142, 144 of the device. Thus, the light emitters associated with the display 480 may thereby be configured to illuminate the first and/or second eye of the user and to display information for the user.

The electronic device 10 may further comprise an eye sensor 146, 148 configured to determine eye characteristics of the first and/or second eye of the user.

For example, in case the eye sensor 146, 148 determines that the eyes of the user are shut, the light emitters 142, 144 may be switched off to conserve power. Eye characteristics may further be used to determine if the user is sleeping.

The controller 112 may be further configured to determine a size of the pupil of the first and/or second eye of the user based on the eye characteristics. The size of the pupil may be determined by an imaging sensor, e.g. a camera.

The controller 112 may be further configured to determine an optical transfer function of the first and/or second eye of the user based on the eye characteristics. The electronic device 10 may comprise additional components, e.g. a tunable laser diode and/or beamsplitters, in order to determine eye characteristics related to the optical transfer function of the first and/or second eye of the user. The optical transfer function may be determined using a double-pass method. The method obtains information about the light that enters the eye, crosses the ocular media, reflects in the fundus and returns. By combining the size of the pupil of the first and/or second eye and the optical transfer function of the first and/or second eye, information related to the amount of light reaching the retina(s) and/or other photoreceptor cells of the first and/or second eye may be improved compared to when using only the size of the pupil or the optical transfer function.

The controller 112 may be further configured to, based on the eye characteristics, determine an identity of the user. For example, the identity of the user may be determined by detecting features of a retina of the eye of the user.

The controller 112 may be further configured to, based on the eye characteristics, adjust the target light profile. For example, in case the eye characteristics indicate that the user is tired, the target light profile may be updated in order to boost the energy of the user. Such an energy boost may be realized by increasing an amount of blue light of the light illuminating the eyes of the user.

The electronic device 10 may further comprise a transceiver 116 configured to communicate with one or more of a server, an external sensor and an external light emitter. For example, the electronic device 10 may retrieve information relating to the user from the server. An example of such information may be the target light profile or updates to the target light profile.

A transceiver 116 configured to communicate with an external light emitter may allow the electronic device 10 to adjust a total light exposure of the user. For example, the electronic device 10 may adjust the first and second light emitters 142, 144 based on information relating to the external light emitter. It is to be understood that the electronic device 10 may adjust an intensity and spectrum of the external light emitter by communicating via the transceiver 116. Thus, the electronic device 10 may adjust the total light exposure of the user by adjusting the first light emitter 142, the second light emitter 144, and the external light emitter.

A transceiver 116 configured to communicate with an external sensor may allow for the electronic device 10 to sense additional data relating to the user. For example, the electronic device 10 may communicate with a continuous blood glucose monitor, which may allow the electronic device 10 to retrieve information relating to a blood glucose level of the user. As a further example, the electronic device 10 may communicate with a sensor monitoring a quality of air, e.g. carbon dioxide levels, in a vicinity of the user. The electronic device 10 may then adjust the first and/or second light emitter 142, 144 based on a sensed quality of air in the vicinity of the user.

The electronic device 10 may further comprise sensors 124, 126 configured to sense one or more of a movement of the user, a position of the user, and a health status of the user. For instance, the movement of the user may be determined by an accelerometer 124. The position of the user may be determined by a gyro, and/or a GPS. By a GPS, the electronic device 10 may determine a global position of the user, and adjust the intensity and spectrum of the first and second light emitter 142, 144 further based on the global position. For instance, a user in a Scandinavian country may need different intensity and spectrum settings of the light emitters 142, 144 than a user in a country in southern Europe do.

Sensors configured to sense the health status of the user may comprise a heart-rate monitor 126 to determine a pulse of the user. It is to be understood that the movement of the user, the position of the user, and the health status of the user may be determined by a combination of a plurality of sensors.

A skilled person realizes that, even though not explicitly depicted in FIG. 1, the electronic device 10 may comprise an internal and/or external power source.

Figure 2:
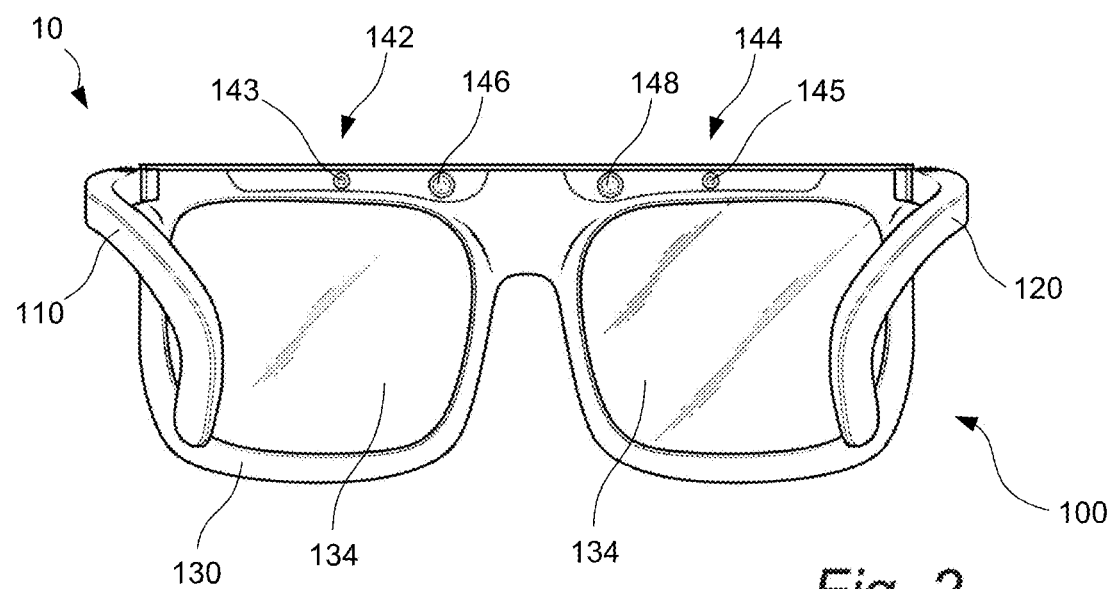
FIG. 2 illustrates an inside of the frame of the electronic device.

FIG. 2 illustrates an inside of the frame 100 of the electronic device 10. As is seen, the first light emitter 142 is configured to illuminate the first eye of the user. The first light emitter 142 comprises a first light source 143. Likewise, the second light emitter 144 is configured to illuminate the second eye of the user. The second light emitter 144 comprises a second light source 145. It is to be understood that the first and/or second light emitters 142, 144 may be positioned in other parts of the rim 130 of the frame 100 than illustrated in FIG. 2. For instance, the first and second light emitter 142, 144 may be positioned in a lower part of the rim 130. It is to be understood that additional light emitters may be mounted to the frame 100. As an example, a third light emitter may be mounted to the frame 100 and configured to illuminate the first eye of the user. In such case, the third light emitter may be mounted at a different position than the first light emitter 142. It is to be understood that a fourth light emitter corresponding to the third light emitter may be mounted to the frame 100 and configured to illuminate the second eye of the user.

The frame 100 may comprise an eye sensor 146, 148. A first eye sensor 146 may be configured to determine eye characteristics of the first eye of the user. A second eye sensor 148 may be configured to determine eye characteristics of the second eye of the user.

Figure 3:
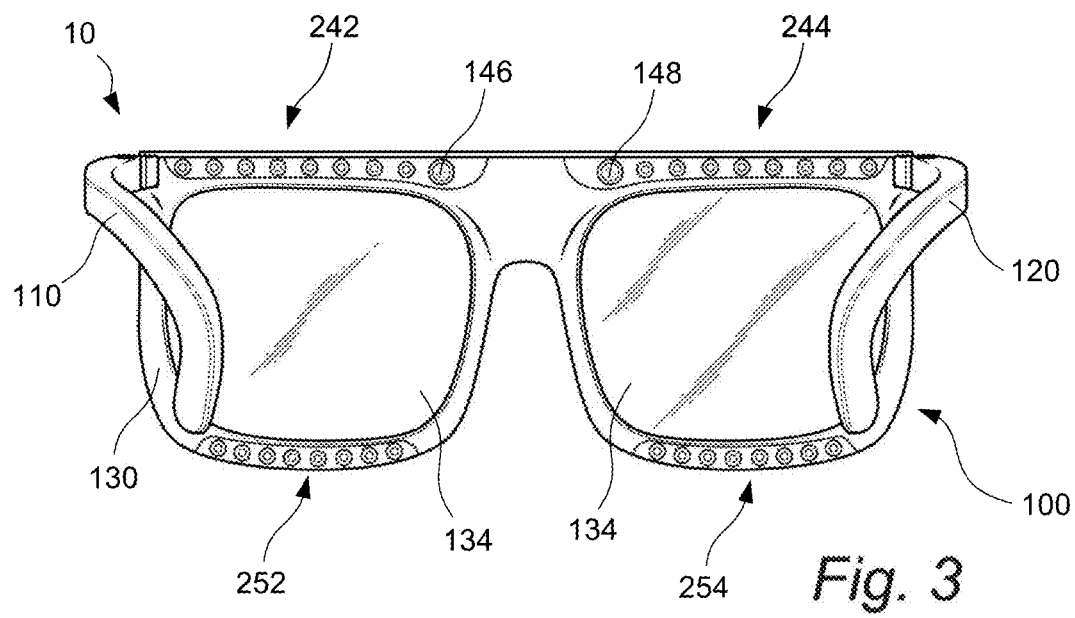
FIG. 3 illustrates an inside of the frame of the electronic device.

FIG. 3 illustrates an alternative arrangement of an inside of the frame 100 of the electronic device 10. As is seen, the first light emitter 242 is configured to illuminate the first eye of the user. The first light emitter 242 comprises a first plurality of light sources. Likewise, the second light emitter 244 is configured to illuminate the second eye of the user. The second light emitter 244 comprises a second plurality of light sources. It is to be understood that spacing between each light source in the first and second plurality of light sources may be smaller or larger than is depicted in FIG. 3.

The light sources in the first and/or second plurality of light sources may be configured to emit light having varying spectra. The light sources in the first and/or second plurality of light sources may be adjustably mounted to the frame 100.

A third light emitter 252, comprising a third plurality of light sources, may be mounted to the frame 100. The third light emitter 252 may be configured to illuminate the first eye of the user. A fourth light emitter 254, comprising a fourth plurality of light sources, may be mounted to the frame 100. The fourth light emitter 254 may be configured to illuminate the second eye of the user. It is to be understood that spacing between each light source in the third and fourth plurality of light sources may be smaller or larger than is depicted in FIG. 3.

The light sources in the third and/or fourth plurality of light sources may be configured to emit light having varying spectra. The light sources in the third and/or fourth plurality of light sources may be adjustably mounted to the frame 100.

Figure 4:
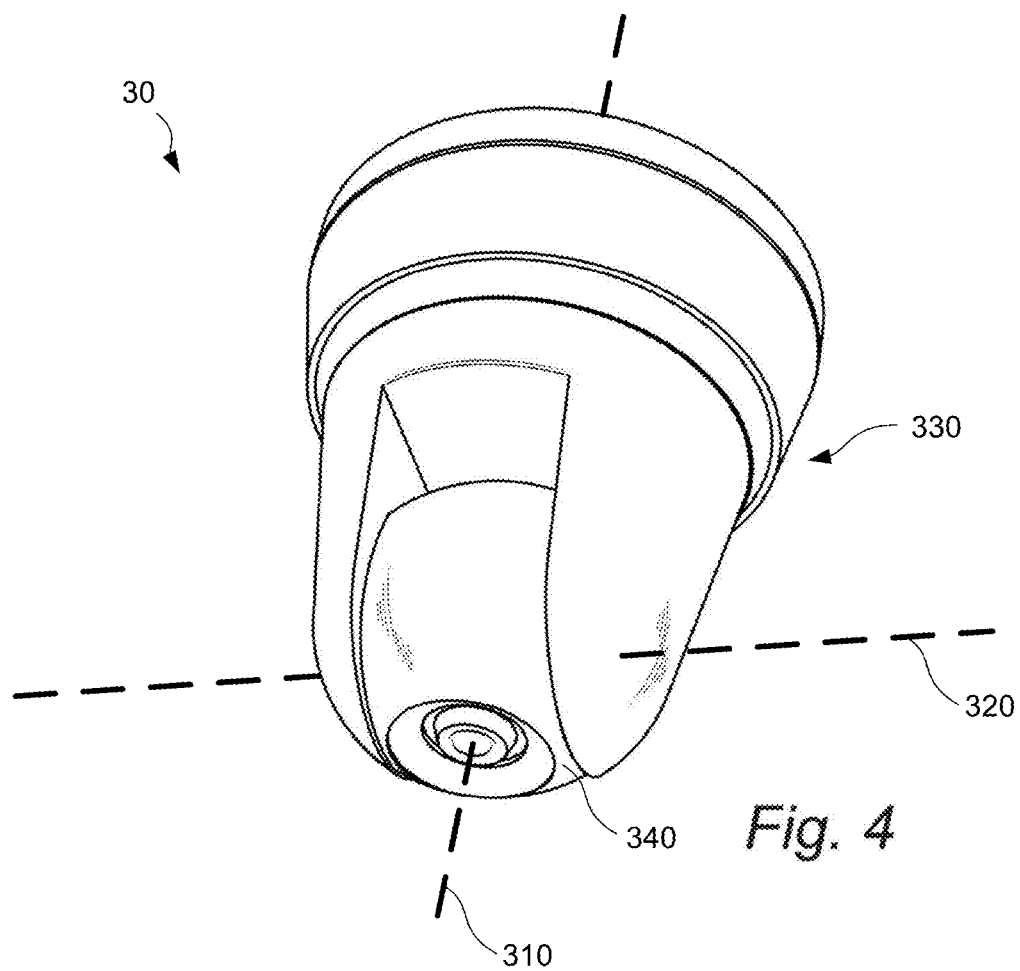
FIG. 4 illustrates a light emitter comprising a light source and a driver.

FIG. 4 illustrates an example of a light emitter 30 comprising a light source 340 and a driver. The driver may be a pan/tilt motor 330 as is seen in FIG. 4. The pan/tilt motor 330 may be configured to rotate the light source 340 about a first axis 310. The pan/tilt motor 330 may be further configured to tilt the light source 340 about a second axis 320. The controller 112 may be further configured to control the rotation and tilt of the pan/tilt motor 330, and the controller 112 may thereby control a direction of light emitted by the light source 340 mounted on the pan/tilt motor 330.

Alternatively, a light emitter may comprise a plurality of light sources arranged in a matrix. Light sources in the plurality of light sources may be light emitting diodes (LEDs). The light sources in the plurality of light sources may be arranged in color groups. The light sources in each color group may be configured to emit light having similar spectra. The light sources in different color groups may be configured to emit light of the different spectra. It is to be understood that the light sources in a color group may be mounted to the frame in a spatially dispersed manner. The light sources in the plurality of light sources may be arranged in directional groups. The light sources in each directional group may be configured to emit light having similar propagation directions. The light sources in different directional groups may be configured to emit light having different propagation directions. It is to be understood that the light sources in a directional group may be mounted to the frame in a spatially dispersed manner. It is to be understood that a light source in the plurality of light sources may simultaneously be arranged in a color group and a directional group. A spectrum light emitted by the light emitter may be controlled by enabling the light sources in one or more of the color groups of the light emitter. A direction of light emitted by the light emitter may be controlled by enabling the light sources in one or more of the directional groups of the light emitter.

A skilled person realizes that positions of the first light emitter 142, the second light emitter 144, the controller 112, the clock 122, the memory 114, the light sensor 132, the optics 134, the eye sensor 146, 148, the transceiver 116, and further sensors indicated in FIG. 1-FIG. 3 are examples only, and may be varied in other variants of present disclosure. For example, the controller 112 may be positioned in the rim 130 instead of in the temple as indicated in FIG. 1.

The electronic device 10 may further comprise a brain sensor 470 configured to determine brain characteristics of the user as exemplified in FIG. 5-FIG. 7. The brain sensor 470 may comprise a plurality of EEG sensors. The EEG sensors may be mounted on the inside of the frame 100, such that the EEG sensors are arranged on the head of the user when the user is wearing the electronic device 10. As is shown in the example in FIG. 5-FIG. 7, the brain sensor 470 may be mounted on the inside of the frame 100 such that the brain sensor 470 is in contact with the forehead of the user (which is exemplified by brain sensor 470a in FIG. 5-FIG. 7) and/or behind the ears of the user (which is exemplified by brain sensor 470b/470c in FIG. 5-FIG. 7). Alternatively, or additionally, the brain sensor 470 may be arranged to be in contact with a temple of the user (not shown in FIG. 5-FIG. 7). It is to be understood that the brain sensor 470 may be arranged to be in contact with other areas of the head of the user.

The controller 112 may be further configured to determine a state of the brain of the user based on the brain characteristics. By measuring the brain waves of the user, the state of the brain may be determined. For instance, the controller may determine if the user has a strongly engaged mind or if the user is daydreaming.

The controller 112 may be further configured to control the first and/or second light emitter 142, 144 based on the brain characteristics. For example, in case the mind of the user is determined to be strongly engaged, the first and/or second light emitter 142, 144 may be adjusted in order to help the user maintain the focus. Alternatively, the controller 112 may use a plurality of different sensors to determine if the first and/or second light emitter 142, 144 need to be adjusted in order for the user to reach a desired state of the brain. For instance, if the controller 112 determines that the user is lying in bed at night (using the clock 122 and a motion sensor/accelerometer 124), and the state of the brain is dominated by beta waves (beta waves are associated with a focused mind), the first and/or second light emitter 142, 144 may be controlled to help the user relax, i.e. affecting the state of the brain to be dominated by alpha waves. Thus, the active and automatic control of the electronic device 10 is improved.

The person skilled in the art realizes that the present inventive concept by no means is limited to the preferred variants described above. On the contrary, many modifications and variations are possible within the scope of the appended claims.

For example, the electronic device 10 described above comprises optics 134, however variants without optics 134 may also be realized.

Furthermore, the direction and or focus of light emitted from a light source may be controlled by a tuneable lens.

Furthermore, the electronic device 10 may comprise additional optics and light emitters arranged such that the electronic device is enabled to display information for the user. The information may relate to the user itself, e.g. information related to health or calendar appointments, or be transmitted to the electronic device 10 (e.g. news flashes, traffic information etc.). The additional light emitters used for displaying the information may further be adjusted in the same manner described above for the first and second light emitter 142, 144.

Additionally, variations to the disclosed variants can be understood and effected by the skilled person in practicing the claimed invention, from a study of the drawings, the disclosure, and the appended claims.

What is claimed is:

1. An electronic device comprising:
a frame configured to be worn on a head of a user;
a first light emitter mounted on the frame and configured to illuminate a first eye of the user, wherein a first intensity and a first spectrum of the first light emitter is adjustable;
a second light emitter mounted on the frame and configured to illuminate a second eye of the user, wherein a second intensity and a second spectrum of the second light emitter is adjustable;
a first driver motor configured to adjust a first direction of the first light emitter;
a second driver motor configured to adjust a second direction of the second light emitter;
a clock configured to determine a time of day;
a memory configured to store a target light profile; and
a controller configured to control the first intensity the second intensity and the first spectrum and the second spectrum of the first light emitter and the second light emitter, respectively, based on the time of day, a circadian rhythm of the user, and the target light profile, such that a first accumulated light exposure and a second accumulated light exposure to the first eye and the second eye, respectively, of the user is aligned with the target light profile over the predetermined timespan;
wherein the target light profile comprises time-resolved data on a first amount of light and a second amount of light and a first angle of incidence and a second angle of incidence to be received by the first eye and the second eye, respectively, of the user over the predetermined timespan,
wherein the controller further controls the first driver motor to control a first direction of light emitted from the first light emitter based on at least one of: the first angle of incidence or the first intensity and the first spectrum of the first light emitter, of the time-resolved data, and wherein the controller further controls the second driver motor to control a second direction of light emitted from the second light emitter based on at least one of: the second angle of incidence, or the second intensity and the second spectrum of the second light emitter, of the time-resolved data.

2. The electronic device according to claim 1, wherein the controller is further configured to individually control the first and second light emitters.

3. The electronic device according to claim 1, wherein the first and/or second light emitter is adjustably mounted on the frame.

4. The electronic device according to claim 1, further comprising:
a light sensor configured to sense ambient light; and
wherein the controller is further configured to adjust the first intensity and the second intensity and the first spectrum and the second spectrum of the first and the second light emitter, respectively, based on the sensed ambient light.

5. The electronic device according to claim 1, further comprising optics mounted to the frame, wherein the optics are configured to filter and/or refract ambient light.

6. The electronic device according to claim 5, wherein the optics comprises a display, wherein an intensity and a spectrum of each of light emitters associated with the display are adjustable; and
wherein the controller is further configured to control the intensity and spectrum of each of the light emitters associated with the display based on the time and the target light profile.

7. The electronic device according to claim 1, further comprising an eye sensor configured to determine eye characteristics of the first and/or second eye of the user.

8. The electronic device according to claim 7, wherein the controller is further configured to, based on the eye characteristics, determine an identity of the user.

9. The electronic device according to claim 8, wherein the controller is further configured to, based on the eye characteristics, adjust the target light profile.

10. The electronic device according to claim 7, wherein the controller is further configured to determine a size of the pupil of the first and/or second eye of the user based on the eye characteristics.

11. The electronic device according to claim 7, wherein the controller is further configured to determine an optical transfer function of the first and/or the second eye of the user based on the eye characteristics.

12. The electronic device according to claim 1, further comprising a transceiver configured to communicate with one or more of:
a server;
an external sensor; and
an external light emitter.

13. The electronic device according to claim 1, further comprising sensors configured to sense one or more of:
a movement of the user;
a position of the user; and
a health status of the user.

14. The electronic device according to claim 1, further comprising a brain sensor configured to determine brain characteristics of the user.

15. The electronic device according to claim 14, wherein the controller is further configured to determine a state of the brain of the user based on the brain characteristics.

16. The electronic device according to claim 14, wherein the controller is further configured to control the first and/or second light emitter based on the brain characteristics.

17. The electronic device according to claim 1, wherein the first driver and the second driver motor comprises a first pan/tilt motor and a second pan/tilt motor, respectively.

18. The electronic device according to claim 17, wherein the controller is further configured to control tilting and rotating the first driver motor and the second driver motor.

19. An electronic device comprising:
a frame configured to be worn on a head of a user;
a first light emitter mounted on the frame and configured to illuminate a first eye of the user, wherein a first intensity and a first spectrum of the first light emitter is adjustable;
a second light emitter mounted on the frame and configured to illuminate a second eye of the user, wherein a second intensity and a second spectrum of the second light emitter is adjustable;
a clock configured to determine a time of day;
a memory configured to store a target light profile;
a controller configured to control the first intensity and the second intensity and the first spectrum and the second spectrum of the first light emitter and the second light emitter, respectively, based on the time of day, a circadian rhythm of the user, and the target light profile, such that a first accumulated light exposure and a second accumulated light exposure to the first eye and the second eye, respectively, of the user is aligned with the target light profile over the predetermined timespan,
wherein the target light profile comprises time-resolved data on a first amount of light and a second amount of light and a first angle of incidence and a second angle of incidence to be received by the first eye and the second eye, respectively, of the user over the predetermined timespan,
wherein the controller is further configured to control direction of light emitted from the first light emitter and the second light emitter based on the time-resolved data on the angle of incidence along with the intensity and the spectrum of the first light emitter and the second light emitter,
wherein the controller is further configured to control a first direction of light emitted from the first light emitter based on at least one of: the first angle of incidence, or the first intensity and the first spectrum of the first light emitter, of the time-resolved data,
wherein the controller is further configured to control a second direction of light emitted from the second light emitter based on at least one of: the second angle of incidence, or the second intensity and the second spectrum of the second light emitter, of the time-resolved data, and
wherein the first light emitter and second light emitter each comprises a plurality of light sources which are arranged in directional groups, the plurality of light sources in different directional groups being configured to emit light in different directions, and the direction of light emitted from the first light emitter and the second light emitter is controlled by enabling the plurality of light sources in the one or more directional groups.

* * * * *